(12) United States Patent
Briska

(10) Patent No.: US 8,679,748 B2
(45) Date of Patent: Mar. 25, 2014

(54) METHODS OF DETERMINING PROPERTIES OF NUCLEIC ACIDS WITHOUT USE OF AN INTERNAL STANDARD AND INVOLVING STRETCH AND OPTICAL INTENSITY

(75) Inventor: Adam M. Briska, Madison, WI (US)

(73) Assignee: OpGen Inc., Gaithersburg, MD (US)

( * ) Notice: Subject to any disclaimer, the term of this patent is extended or adjusted under 35 U.S.C. 154(b) by 520 days.

(21) Appl. No.: 12/465,392

(22) Filed: May 13, 2009

(65) Prior Publication Data

US 2010/0028886 A1   Feb. 4, 2010

Related U.S. Application Data

(60) Provisional application No. 61/127,653, filed on May 14, 2008.

(51) Int. Cl.
*C12Q 1/68*   (2006.01)

(52) U.S. Cl.
USPC .......................................................... 435/6.1

(58) Field of Classification Search
USPC .......................................................... 435/6.1
See application file for complete search history.

(56) References Cited

U.S. PATENT DOCUMENTS

| | | | |
|---|---|---|---|
| 6,340,567 B1 * | 1/2002 | Schwartz et al. | 435/6 |
| 7,049,074 B2 * | 5/2006 | Schwartz | 435/6 |
| 2002/0081744 A1 | 6/2002 | Chan et al. | |
| 2003/0124611 A1 | 7/2003 | Schwartz | |
| 2006/0155483 A1 * | 7/2006 | Antoniotti et al. | 702/20 |
| 2007/0037152 A1 | 2/2007 | Drmanac | |
| 2007/0082358 A1 * | 4/2007 | Fuerst et al. | 435/6 |
| 2007/0092905 A1 * | 4/2007 | Gimzewski et al. | 435/6 |

OTHER PUBLICATIONS

The International Search Report and the Written Opinion of the International Searching Authority from corresponding PCT application No. PCT/US2009/043719, dated Jul. 6, 2009 (13 pages).
International Preliminary Report on Patentability in corresponding PCT application No. PCT/US2009/043719, mailed Jul. 6, 2009, 8 pages.
Supplemental European Search Report for European application No. 09747423.3, 6 pages, Feb. 21, 2012.
Schwartz et al., Science, 262(5130):110-114, 1993.
Jing et al., Proc. Natl. Acad. Sci. USA, 95:8046-8051, 1998.

* cited by examiner

*Primary Examiner* — Kenneth Horlick
(74) *Attorney, Agent, or Firm* — Thomas C. Meyers; Brown Rudnick LLP

(57) ABSTRACT

This disclosure features, inter alia, methods for determining at least one property of a nucleic acid. The methods include: (a) fixing the nucleic acid on a planar surface; (b) digesting the nucleic acid into fragments with at least one enzyme; (c) imaging the nucleic acid; and (d) analyzing the imaged nucleic acid to determine the property of the nucleic acid, wherein no internal nucleic acid standard is added during the method.

18 Claims, 1 Drawing Sheet

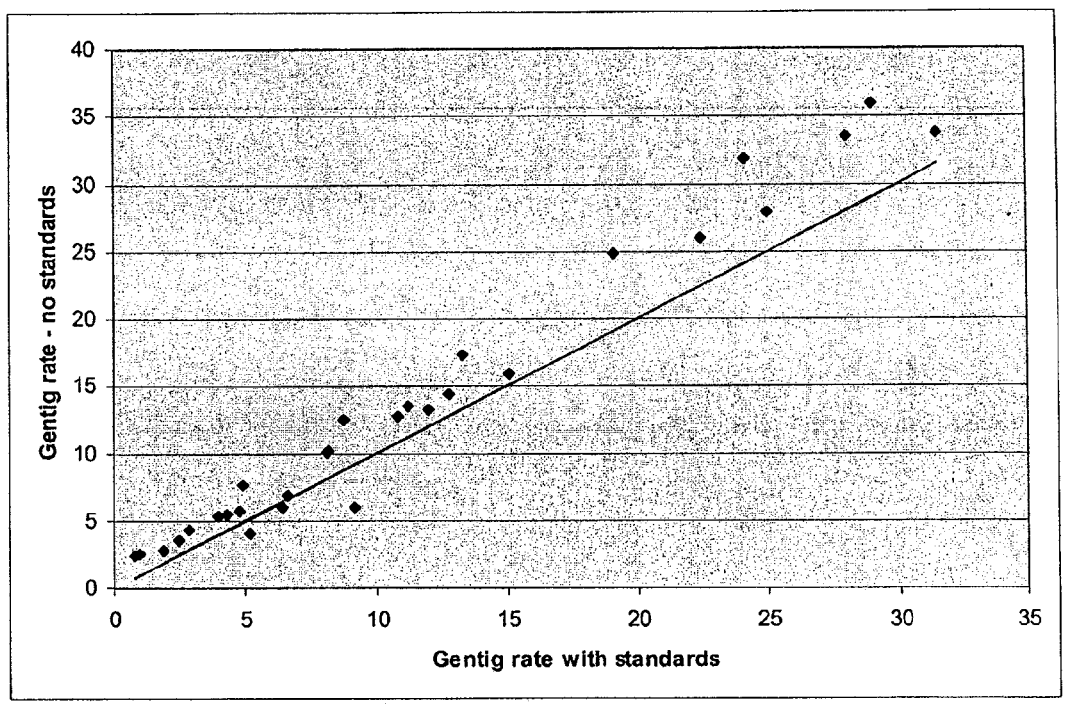

US 8,679,748 B2

METHODS OF DETERMINING PROPERTIES OF NUCLEIC ACIDS WITHOUT USE OF AN INTERNAL STANDARD AND INVOLVING STRETCH AND OPTICAL INTENSITY

RELATED APPLICATION

The present application is related to and claims the benefit of U.S. provisional patent application Ser. No. 61/127,653, filed May 14, 2008, the contents of which are incorporated herein by reference in their entirety.

TECHNICAL FIELD

This disclosure relates to methods of determining a property, e.g., size, of a molecule, e.g., a nucleic acid, without use of an internal standard.

BACKGROUND

Physical mapping of genomes, e.g., using restriction enzymes to develop restriction maps, can provide accurate information about the nucleic acids of various organisms. Restriction maps of, e.g., deoxyribonucleic acid (DNA), can be generated by optical mapping. Optical mapping can produce ordered restriction maps by using fluorescence microscopy to visualize restriction endonuclease cutting events on individual labeled DNA molecules. Generally, internal standards are used to size the nucleic acid molecules digested by restriction enzymes.

SUMMARY

The present disclosure features, inter alia, methods of determining at least one property of a molecule, e.g., a nucleic acid or nucleic acid fragment. Methods can be used for restriction mapping, e.g., optical mapping. In a preferred embodiment, methods of the invention allow size determination of a nucleic acid without the use of an internal standard or control. When the nucleic acid being sized is DNA, the methods do not require prior knowledge of a reference genome. The methods also do not require modification of the source molecule. When the nucleic acid is fluorescently labeled, its size is determined, inter alia, by the following formula: (pixel length of the nucleic acid)/(known stretch–kb/pixel)×(fluorescence of a fragment)/(fluorescence of the nucleic acid). Use of methods of the invention result in decreased complexity and increase efficiency of nucleic acid sizing.

Further aspects and features of the invention will be apparent upon inspection of the following detailed description thereof.

All patents, patent applications, and references cited herein are incorporated in their entireties by reference.

BRIEF DESCRIPTION OF THE DRAWINGS

FIG. 1 is a graph showing on the X axis the gentig rate (percent of usable molecules) obtained with use of internal standards and on the Y axis the gentig rate obtained without an internal standard.

DETAILED DESCRIPTION

The present disclosure features, inter alia, methods of determining at least one property of a molecule, e.g., size of a nucleic acid or sizes of nucleic acid fragments. The methods can be used during restriction mapping, e.g., optical mapping. The methods allow for such size determination without the use of an internal standard or control. When the nucleic acid being sized is DNA, the methods do not require prior knowledge of a reference genome. The methods also do not require modification of the source molecule, e.g., a nucleic acid. When the nucleic acid is fluorescently labeled, its size is determined, inter alia, by the following formula: (pixel length of the nucleic acid)/(known stretch–kb/pixel)×(fluorescence of a fragment)/(fluorescence of the nucleic acid). The featured methods can decrease the complexity and increase efficiency of nucleic acid sizing.

Restriction Mapping

The methods featured herein can be used during restriction mapping. Exemplary types of restriction mapping that can be used are optical mapping and/or optical sequencing.

Optical mapping is a single-molecule technique for production of ordered restriction maps from a single DNA molecule (Samad et al., *Genome Res.* 5:1-4, 1995). Various methods can be used for controllable elongation of single nucleic acid molecules in optical mapping and/or sequencing. The methods can be gel-based, solid surface-based, and flow-based (see, e.g., U.S. Pat. No. 6,509,158).

During some applications, individual fluorescently labeled DNA molecules are elongated in a flow of agarose between a coverslip and a microscope slide (in a first-generation method) or fixed onto polylysine-treated glass surfaces (in a second-generation method). Samad et al. supra. The added endonuclease cuts the DNA at specific points, and the fragments are imaged. Id. Restriction maps can be constructed based on the number of fragments resulting from the digest. Id. Generally, the final map is an average of fragment sizes derived from similar molecules. Id.

Optical mapping and related methods are described in U.S. Pat. Nos. 5,405,519, 5,599,664, 6,150,089, 6,147,198, 5,720,928, 6,174,671, 6,294,136, 6,340,567, 6,448,012, 6,509,158, 6,610,256, and 6,713,263. All the cited patents are incorporated by reference herein in their entireties.

Use of Standards During Restriction Mapping

Various types of internal standards/references can be used during restriction mapping. One type of a standard is an internal fluorescence standard consisting of a reference DNA molecule of known sequence. The reference DNA molecule is co-mounted and used to calculate a standard measure of integrated fluorescence intensity per kilobase of DNA, based on an established formula (Li et al., *J. Comput. Biol.* 14 (3):255-66, 2007). Another type of a standard is a sequence from a reference genome that has been digested with restriction endonuclease(s) (i.e., a reference map). Id.

The use of standards adds steps to restriction mapping methods, e.g., steps of digesting the standard with specific enzymes, pairing the standard with the sample, and/or re-prepping the sample that require multiple enzyme digests or change of enzymes. Using standards also requires additional reagents, e.g., restriction enzymes for digesting a standard.

The methods featured herein do not require the use of an internal standard. When the nucleic acid being sized is DNA, the methods do not require prior knowledge of a reference genome. The methods also do not require modification of the source nucleic acid, e.g., DNA.

The methods featured herein are based, inter alia, upon the empirical observation that the molecules deposited on the surface are consistently stretched. Without being bound by theory, it is believed that because of controlled fluid flow conditions, the resulting deposited molecules have a generally consistent force applied to them, which produces a generally consistent stretch across various molecule preparations, e.g., a nucleic acid, e.g., a deoxyribonucleic acid, preparations. Thus, the methods rely, among others, upon the repeatable physical properties of the system for size determination. Based upon the known stretch, when the nucleic acid is fluorescently labeled, its size is determined, inter alia, by the following formula: (pixel length of the nucleic acid)/(known stretch–kb/pixel)×(fluorescence of a fragment)/(fluorescence of the nucleic acid).

Thus, by removing the requirement of an internal sizing standard, the methods featured herein reduce the complexity of sample preparation, e.g., automatic sample preparation, and expand the list of possible enzymes that can be used in digestion of the molecule being analyzed.

Applications

Restriction mapping, e.g., optical mapping, without the use of internal standards, can be used in a variety of applications. For example, the methods featured herein can be used to determine a property, e.g., physical and/or chemical property, e.g., size, length, restriction map, weight, mass, sequence, conformational or structural change, pKa change, distribution, viscosity, rates of relaxation of a labeled and/or non-labeled molecule, e.g., an amplicon (e.g., PCR product), of a portion of a genome (e.g., a chromosome), or of an entire genome.

The methods can also be used to identify various organisms, e.g., viruses and prions, and various microorganisms, e.g., bacteria, protists, and fungi, whose genetic information is stored as DNA or RNA by correlating the restriction map of a nucleic acid of an organism with a restriction map database. Such identification methods can be used in diagnosing a disease or disorder. Methods of identifying organisms by restriction mapping are described, e.g., in a U.S. Patent Application Ser. No. 61/029,816, filed on Feb. 19, 2008, incorporated herein by reference.

The methods featured herein can also be used in other diagnostic applications, for example, imaging specific loci or genetic regions for individuals or populations to help identify specific diseases or disorders.

Other uses of the methods will be apparent to those skilled in the art.

The following example provides an illustrative embodiment of the present methods and should not be treated as restrictive.

EXAMPLE 1

Sizing DNA Without Internal Standards

A DNA sample was deposited, elongated, and fixed on a planar surface. The DNA was fluorescently labeled and digested into fragments with restriction endonucleases. The sample was imaged under a fluorescent microscope. The sizes of the fragments were analyzed in two ways. First, the fragments were compared to a standard sample digested with the same enzymes. Second, the following formula was used to determine fragment size:

fragment size=(pixel length of the nucleic acid)/
(known stretch–kb/pixel)×(fluorescence of a
fragment)/(fluorescence of the nucleic acid).

DNA from the organisms *E. coli, Z. mobilis, R. opacus*, and *S. aureus* was deposited on derivatized glass surfaces using capillary action in a microfluidic device. These DNA samples were then digested with the restriction enzymes AflII, BamHI, BglII, EagI, NcoI, and NdeI.

The gentig rate (percentage of usable molecules based the Gentig algorithm created to deal with the types of errors unique to the analysis of single DNA maps) of the sizing method utilizing the standards was compared against the gentig rate obtained with the above formula. The results are presented in FIG. 1. The X axis represents the gentig rate with internal standards and the Y axis represents the gentig rate without standards. The solid line indicates the graph y=x, and each point represents data from a single Optical Chip. The points above the line indicate improved performance. The graph shows that the method utilizing the formula above without the internal standards resulted in increased performance.

An additional step that will be implemented will involve correcting for different sizing biases in differently sized fragments, because occasionally different fluorescence characteristics can appear for fragments of different sizes. In this step, the fluorescence intensity profile will be analyzed along the length of the molecule. First, a backbone value, which corresponds to all regions on the molecule that are "internal" to a fragment, will be identified.

These "internal" regions will be constrained by the distance from an edge of a fragment and by a flat intensity profile. Once these internal regions are defined, a function will be fitted to resulting intensity profile graph. Finally, for each interval between internal sections, the fluorescence intensity will be normalized such that it will match the integral of the function along this same region.

The embodiments of the disclosure may be carried out in other ways than those set forth herein without departing from the spirit and scope of the disclosure. The embodiments are, therefore, to be considered to be illustrative and not restrictive.

What is claimed is:

1. A method for determining at least one property of a nucleic acid, the method comprising:
   (a) fixing the nucleic acid on a planar surface;
   (b) digesting the nucleic acid into fragments with at least one enzyme;
   (c) imaging the nucleic acid; and
   (d) analyzing a relationship between known stretch of a nucleic acid fragment and optical intensity of the fragment to determine the property of the nucleic acid, wherein no internal nucleic acid standard is added during the method.

2. The method of claim 1, wherein the imaging step comprises fluorescently labeling the nucleic acid.

3. The method of claim 2, wherein said property is a size of at least one fragment of the nucleic acid.

4. The method of claim 3, wherein the size of the fragment of the nucleic acid is determined by the following formula: (pixel length of the nucleic acid)/(known stretch–kb/pixel)×(fluorescence of a fragment)/(fluorescence of the nucleic acid).

5. The method of claim 2, wherein the analyzing step further comprises identifying a backbone fluorescence intensity for the fragments, obtaining an intensity profile, and normalizing the fluorescence intensity among the fragments, thereby correcting for sizing biases of the fragments.

6. The method of claim 5, wherein the intensity profile is expressed as a graph.

7. The method of claim 1, wherein said nucleic acid is deoxyribonucleic acid.

8. The method of claim 1, wherein said nucleic acid is ribonucleic acid.

9. The method of claim 1, wherein said nucleic acid is a human nucleic acid.

10. A method for constructing an ordered restriction map, the method comprising:
    (a) fixing a nucleic acid on a planar surface;

(b) digesting the nucleic acid into fragments with at least one enzyme;
(c) imaging the nucleic acid;
(d) analyzing a relationship between known stretch of a nucleic acid fragment and optical intensity of the fragment; and
(e) constructing an ordered restriction map based upon results of step (d), wherein no internal nucleic acid standard is added during the method.

11. The method of claim 10, wherein the imaging step comprises fluorescently labeling the nucleic acid.

12. The method of claim 11, wherein the analyzing step comprises sizing of the fragments of the nucleic acid.

13. The method of claim 12, wherein the sizing of the fragments of the nucleic acid is determined by the following formula: (pixel length of the nucleic acid)/(known stretch–kb/pixel)×(fluorescence of a fragment)/(fluorescence of the nucleic acid).

14. The method of claim 11, wherein the analyzing step further comprises identifying a backbone fluorescence intensity for the fragments, obtaining an intensity profile, and normalizing the fluorescence intensity among the fragments, thereby correcting for sizing biases of the fragments.

15. The method of claim 14, wherein the intensity profile is expressed as a graph.

16. The method of claim 10, wherein said nucleic acid is deoxyribonucleic acid.

17. The method of claim 10, wherein said nucleic acid is ribonucleic acid.

18. The method of claim 10, wherein said nucleic acid is a human nucleic acid.

* * * * *